United States Patent [19]

Vishnuvajjala et al.

[11] Patent Number: 4,943,579
[45] Date of Patent: Jul. 24, 1990

[54] WATER SOLUBLE PRODRUGS OF CAMPTOTHECIN

[75] Inventors: B. Rao Vishnuvajjala, Rockville, Md.; Aaron Garzon-Aburbeh, St. Louis Park, Minn.

[73] Assignee: The United States of America as represented by the Secretary of the Department of Health and Human Services, Washington, D.C.

[21] Appl. No.: 104,894

[22] Filed: Oct. 6, 1987

[51] Int. Cl.$^5$ .................... A61K 31/47; C07D 491/22
[52] U.S. Cl. ........................... 514/283; 514/81; 546/23; 546/48
[58] Field of Search ............ 546/48, 23; 514/283, 514/81

[56] References Cited

U.S. PATENT DOCUMENTS

| | | | |
|---|---|---|---|
| 3,894,029 | 7/1975 | Winterfeldt et al. | 546/48 |
| 3,903,276 | 9/1975 | Nudelman et al. | 514/221 |
| 3,966,713 | 6/1976 | Hofmeister et al. | 260/397.45 X |
| 4,031,098 | 6/1977 | Sugasawa | 546/48 |
| 4,160,827 | 7/1979 | Cho et al. | 548/338 X |
| 4,301,285 | 11/1981 | Stein | 544/138 |
| 4,399,276 | 8/1983 | Miyasaka et al. | 546/48 |
| 4,399,282 | 8/1983 | Miyasaka et al. | 546/48 |
| 4,440,764 | 4/1984 | Nathansohn et al. | 514/176 |
| 4,473,692 | 9/1984 | Miyasaka et al. | 546/48 |
| 4,482,722 | 11/1984 | Thorbek et al. | 548/338 |
| 4,513,138 | 4/1985 | Miyasaka et al. | 546/48 |
| 4,545,880 | 10/1985 | Miyasaka et al. | 204/158 R |
| 4,548,819 | 10/1985 | De Clercq et al. | 514/261 |
| 4,604,463 | 8/1986 | Miyasaka et al. | 544/125 |
| 4,694,006 | 9/1987 | Bundgaard et al. | 544/243 |

FOREIGN PATENT DOCUMENTS

| | | | |
|---|---|---|---|
| 088642 | 9/1983 | European Pat. Off. | |
| 116074 | 9/1982 | Japan | |
| 0195344 | 8/1987 | Japan | 546/23 |
| 0195393 | 8/1987 | Japan | 546/23 |

OTHER PUBLICATIONS

Gottlieb, et al, *Cancer Chemo. Therapy Reports* Part 1, 54 (6): 461–470 (1970).
Moertel, et al. *Cancer Chemo. Therapy Reports*, Part 1, 56 (1): 95–101 (1972).
Gottlieb, et al. *Cancer Chemo. Therapy Reports* Part 1, 56 (1): 103–105 (1972).
Vishnuvajjala, et al. *Pharmaceutical Research* 3 (5): 22S (1986, Supplement).
Repta, et al., J. Pharm. Soc., vol. 64, 392 (1975).
Varia, et al., Chemical Abstracts, vol. 101: 183376y (1984).
Varia, et al. (T), Chemical Abstracts, vol. 101: 230412u (1984).
Bundgaard, et al., Int. J. Pharm., vol. 18, 67 (1984).

*Primary Examiner*—Diana G. Rivers
*Attorney, Agent, or Firm*—John Bailey; Robert Benson

[57] ABSTRACT

Water-soluble derivatives of camptothecin have the formulae:

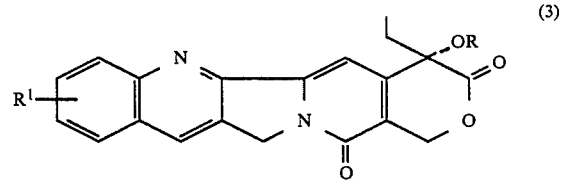

(3)

wherein R' is selected from the group consisting of
R=CO CH$_2$NH$_2$.HCl
R=CO CH$_2$NHCH$_3$.HCl
R=CO CH$_2$NHC$_2$H$_5$.HCl
R=CO CH$_2$ N(C$_2$H$_5$)$_2$.HCl
R=CO CH(NH$_2$) CH$_2$CH$_2$CH$_2$CH$_2$CH$_2$NH$_2$.2HCl
R=CO CH(NH$_2$) CH$_2$CH$_2$COOH. HCl
R=CO CH$_2$CH$_2$.COO$^-$ Na$^+$
R=HPO$_3^-$ Na$^+$ 3 Claims, No Drawings

WATER SOLUBLE PRODRUGS OF CAMPTOTHECIN

FIELD OF THE INVENTION

The present invention is directed to water-soluble derivatives of camptothecin.

BACKGROUND OF THE INVENTION

Camptothecin is a cytotoxic alkaloid first isolated by Wall and his coworkers (*J. Am. Chem. Soc.* 88 3888, 1966) from leaves and barks of *Camptotheca accuminata* (NYSSACEAE), a plant native to China. This alkaloid has a pentacyclic structure consisting of a fused ring system of quinoline rings (rings A and B), a pyrrolidine ring (ring C), an alpha-pyridone ring (ring D), and a six-membered lactone ring (ring E). The compound displays dextro-rotation due to the S-configuration of a tertiary hydroxy group in the 20-position. Earlier reports on the carcinostatic activity of camptothecin were based on inhibitor activity toward an experimentally transplanted carcinoma such as leukemia L-1210 in mice, or Walker 256 tumor in rats (Chem. Rev. 23 (1973), 385; Cancer Treat. Rep., 60 (1967), 1007] stimulated synthetical researches on camptothecin, but the subsequent biological evaluation in the reports indicated that this compound is highly toxic and consequently is unusable as a chemotherapeutic agent. Hemorrhagic enterocolitis was the major dose-limiting toxic effect of the drug in preclinical studies in the beagle and rhesus monkey. Minimal hepatotoxicity and moderate eosinophilia and bone marrow depression were also noted.

Camptothecin is practically insoluble in aqueous vehicles that are suitable for parenteral administration. Therefore, it becomes necessary to modify the chemical structure of the alkaloid to make it water soluble. Sodium camptothecin (Formula 2), obtained by opening the lactone ring of the parent compound with sodium hydroxide, has excellent solubility properties, (>50 mg/ml in water), and therefore received much of the attention in the preclinical and clinical stages. However, as reported in Gottlieb et al., *Cancer Chemother. Rep.* 54, 461 (1970), Moertel et al., ibid, 56, 95 (1972); Gottlieb et al., ibid, 56, 103 (1972), the early clinical studies with this agent were disappointing. The sodium salt displayed unexpected toxicity that precluded achievement of therapeutically useful doses.

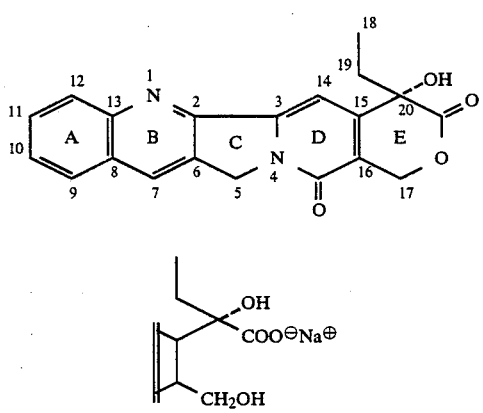

Despite these clinical setbacks, interest in camptothecin as an anti-tumor agent has remained very high. Careful evaluation of these agents in animal models revealed that the sodium salt is only 10–20% as potent as the parent camptothecin [Wani et al., *J. Med. Chem.* 23, 554 (1980)]. In addition, important parameters for anti-tumor activity in the camptothecin series have been established [Wall et al., *Ann. Rev. Pharmacol. Toxicol.* 17, 117 (1977)]. These studies revealed that the intact lactone ring, ring E, and hydroxyl group at position 20 are essential for antitumor activity.

Clearly, there is a need to obtain camptothecin in a water-soluble form while retaining the structural elements (i.e., 20-hydroxyl and ring E lactone) that are essential for its pharmacological activity.

A number of attempts have heretofore been made to provide more active derivatives of camptothecin, but none of these compounds has been disclosed to be more water soluble than the parent drug.

Miyasaka et al., U.S. Pat. No. 4,399,282, disclose camptothecin derivatives which are said to have either high anti-tumor activity or low toxicity, wherein the 7-hydroxymethyl group is converted into a 7-alkoxymethyl group or a 7-acyloxymethyl group with or without simultaneous acylation of the 20-hydroxyl group. There is no disclosure that acylation of the 20-hydroxyl group provides camptothecin derivatives which are water-soluble. Winterfeldt et al., U.S. Pat. No. 3,894,029, disclose compounds of the formula:

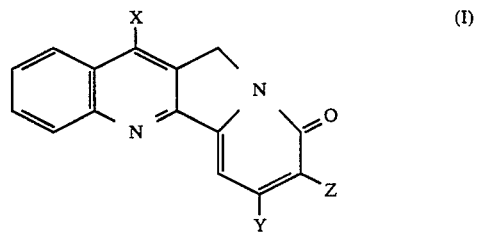

where
X is hydrogen, chlorine, bromine, alkoxy, or dialkylamino;
Y is —CH(COOR)$_2$;
Z is —CH$_2$OH;
Y and Z together are

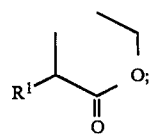

wherein R$^2$ is ethyl. There is no disclosure that this ethyl group in the 20-position increases the water solubility of the compound.

Japanese Pat. No. 57-116074 discloses camptothecins of the following formula:

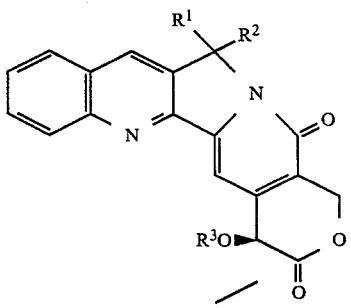

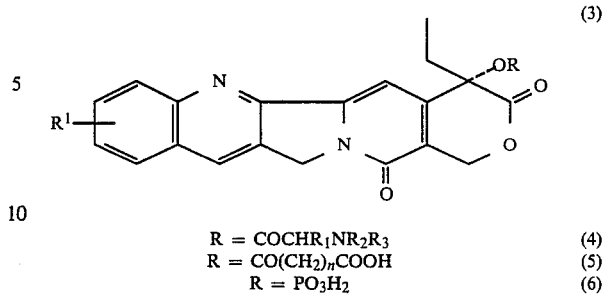

| | |
|---|---|
| R = COCHR₁NR₂R₃ | (4) |
| R = CO(CH₂)ₙCOOH | (5) |
| R = PO₃H₂ | (6) | wherein $R^3$ is lower alkyl or acyl. These compounds are said to be less toxic and more active against leukemia L-1210 in mice. However, there is no indication that these compounds are more soluble in water.

SUMMARY OF THE INVENTION

It is an object of the present invention to overcome the above-noted deficiencies of the prior art.

It is another object of the present invention to convert camptothecin to water-soluble derivatives thereof.

It is a further object of the present invention to provide an improved method of treating certain types of cancers.

It is still another object of the present invention to provide prodrugs of camptothecin.

According to the present invention, camptothecin is converted into water soluble molecules, hereinafter called prodrugs, which, when introduced into the bloodstream of patients, are readily converted to the parent drug, camptothecin.

Conversion of the prodrugs to camptothecin is mediated by a group of enzymes called esterases that are present in the blood of many animals, including humans. Since the prodrugs are rapidly distributed throughout the body within a short period of time after delivery, these prodrugs exist at a very low concentration at the time they undergo enzymatic hydrolysis. This prevents camptothecin from precipitating in the blood stream.

The prodrugs of the present invention are prepared by converting camptothecin to the corresponding 20-O-esters using coupling reaction with molecules containing additional ionizable functional groups that are then converted to the appropriate water soluble salts.

Although the prodrug approach has been previously used for improving the aqueous solubility of drugs, as, for example, Bundgard et al., *Int. J. Pharm.* 18, 67, 1984; Repta et al., *J. Pharm. Soc.*, 64, 392, 1975. however, the present invention is the first time this approach has been used with camptothecin and related structures.

The present invention was first referred to in an abstract in *Pharmaceutical Research*, volume 3, number 5, October, 1986 (Supplement) p. 225, which abstract is incorporated herein by reference.

DETAILED DESCRIPTION OF THE INVENTION

The present invention relates to pharmaceutically active salts prepared from camptothecin derivatives (prodrugs) which are characterized by the general formula 3, and by the specific formulae 4, 5, and 6.

In formula 4, when $R_2$ and $R_3$ represent hydrogen atoms, $R_1$ represents either a hydrogen atom or an alkyl group, whether substituted or not, and such as those found in appropriate natural amino acids. When $R_1$ is a hydrogen atom, $R_2$ and $R_3$ maybe either hydrogen atoms or substituted or unsubstituted alkyl groups, the same or independent of each other. In formula 5, n represents the number of methylene groups that can vary from 1 to 5.

From among these formulae, structures represented by formula 3 where:

| | |
|---|---|
| R = COCH₂NH₂·HCl | (7) |
| R = COCH₂NHCH₃·HCl | (8) |
| R = COCH₂NHC₂H₅·HCl | (9) |
| R = COCH₂N(C₂H₅)₂·HCl | (10) |
| R = COCH(NH₂)CH₂CH₂CH₂CH₂CH₂NH₂·2HCl | (12) |
| R = COCH(NH₂)CH₂CH₂COOH·HCl | (13) |
| R = COCH₂CH₂·COO⁻Na⁺ | (14) |
| R = HPO₃⁻Na⁺ | (15) | are preferred because of their significant anti-tumor activity, adequate water solubility, and ready reversal to camptothecin in the presence of either human or murine plasma.

Table 1 represents the aqueous solubility and the anti-tumor activity of these compounds. The anti-tumor testing was carried out in CDF-1 mice in which were implanted L-1210 lymphoid leukemia, and the drug is delivered intraperitoneally on a schedule of QD4X2.

TABLE 1

| Aqueous solubility and Anti-Tumor Activity (IP/IP,QD4 × 2) | | |
|---|---|---|
| Compound | Solubility (mg/ml) | Dose/Injection (mg/Kg) | T/C % |
| Camptothecin | 0.05 | 8 | 197 |
| Formula 7 | 6 | 15 | 162 |
| Formula 8 | 4 | 30 | 191 |
| Formula 9 | 8 | 30 | 170 |
| Formula 10 | 5 | 30 | 256 |
| Formula 12 | 15 | 50 | 253 |
| Formula 13 | 6 | 50 | 154 |
| Formula 14 | 13 | 47 | 200 |
| Formula 15 | 8 | 44 | 192 |

Table 2 shows the in vitro plasma hydrolysis of the above-described compounds. The data are shown to reflect the relative hydrolysis rates as measured by $t_{\frac{1}{2}}$, the time required for the concentration of the drug to become one half of the starting concentration. Freshly obtained samples of human and murine plasma were used in these studies. The study demonstrated that the prodrugs are converted to the parent drug, camptothecin, within a reasonable period of time after introduction into systemic circulation.

TABLE 2

Rate of hydrolysis of prodrugs in human and murine plasma[a]

| Compound | Human Plasma t½, min | Murine Plasma t½, min |
|---|---|---|
| Formula 7 | 15 | 36 |
| Formula 8 | 13 | 28 |
| Formula 9 | 18 | 40 |
| Formula 10 | 45 | N.D.[b] |
| Formula 12 | 20 | 48 |
| Formula 13 | 18 | 35 |
| Formula 14 | 16 | 40 |
| Formula 15 | 20 | 27 |

[a]Initial drug concentration (50 mcg/ml)
[b]N.D. — Not Determined

The prodrug esters of camptothecin can be prepared as described below.

Camptothecin is suspended in methylene chloride or other inert solvent, stirred, and cooled to 4° C., to which mixture are added one equivalent of the reacting acid of the general formula HOOC $CHR_4NR_5R_6$, one equivalent of dicyclohexylcarbodiimide (DCC), and one tenth of an equivalent of 4-dimehylaminopyridine (DMAP). The mixture is stirred for one hour and is then allowed to come to room temperature. At the end of six hours, dicyclohexyl urea which has precipitated is removed by filtration, the filtrate washed with water, and the product isolated after removal of solvent. The free base of the aminoester thus obtained is converted to the appropriate salt, preferably the hydrochloride salt. The salt is purified by crystallization from a suitable solvent. This procedure is applicable only wherein $R_5$ and $R_6$ both represent alkyl groups and $R_4$ represents either a hydrogen or alkyl group in the above general formula for the reacting carboxylic acid.

If the desired prodrugs contain either a primary $R_2=R_3=H$, as in Formula 4, or a secondary amine function ($R_2=H$, $R_3=$alkyl, formula 4), or if $R_1$ in formula 4 represents an alkyl group substituted with either an $NH_2$ group or a COOH group, such as those found in lysine and glutamic acid, respectively, then it is necessary to protect all of the additional functional groups of the reacting carboxylic acid before the DCC coupling reaction. Generally, the primary or secondary amines are protected with either a t-butyloxycarbonyl (t-BOC) or a carbobenzyloxy (CBZ) group, and the additional carboxylic acid groups are selectively protected as t-butyl esters. The procedures for such protections are common, and are well known by one skilled in the art of organic synthesis.

When the reacting carboxylic acids of the general formula $HOOCCHR_4NR_5R_6$ contain such protecting groups, the coupling reaction with camptothecin can still be carried out using DCC and DMAP as described above. The products isolated form these reactions contain protected amino or carboxylic acid function which must be deblocked before the desired products are obtained. This can be accomplished as follows:

The protected camptothecin esters are dissolved in a mixture of trifluoroacetic acid and methylene chloride, usually in a 1:1 ratio, and stirred at room temperature. Typically, the deblocking reaction requires about an hour or so. The products are isolated by evaporation to the solvents, and then converted to water soluble salts, such as the hydrochloride salt or the sodium salt as appropriate.

Prodrug esters of camptothecin containing an N-substituted glycine moiety (formula 4, where $R_1=H$, $R_2=H$ or alkyl, $R_3=$alkyl) may be prepared equally efficiently using an alternate procedure as described below:

Camptothecin is first converted to 20-O-chloroacetate (formula 3, $R'=H$, $R=COCH_2Cl$) with chloroacteic anhydride, pyridine, and DMAP. The chloroacetate is then converted to the iodoacetate, formula 3, where $R=COCH_2I$, using either NaI or KI, and the iodoacetate is converted to the desired glycinates by reaction with various commonly available primary or secondary amines. These will results in either mono- or di-substituted glycinates of camptothecin.

Compounds represented by formula 5 can be prepared by a direct reaction between camptothecin and an appropriate dicarboxylic acid. DCC can be used as a coupling agent, and DMAP can be used as a catalyst as described above. The resulting product will have an ionizable carboxylic acid function that can be readily converted to a water soluble salt by the addition of a base such as NaOH.

Camptothecin 20-O-phosphate, formula 6, can be prepared by reaction between camptothecin and pyrophosphoryl tetrachloride under conditions similar to those described by Cho et al., *J. Pharm. Sci.* 71, 410, 1982. The resulting intermediate is hydrolyzed by water and converted to the monosodium salt by titration with NaOH to pH 7.5.

The following non-limiting examples illustrate methods for preparing the compounds of the present invention.

Example 1

Camptothecin-20-O-glycinate.HCl (Formula 7)

A mixture of 100 mg, 0.287 mole camptothecin, 50.3 mg, 0.287 mole N-t-butyl glycine, 62 mg, dicyclohexylcarbodiimide (DCC), and 3.6 mg, BOC dimethylaminopyridine (DMAP) was suspended in 100 ml of dry methylene chloride and stirred for one hour at 4° C. The mixture was allowed to come to room temperature, and the stirring was continued for six hours. The mixture was then filtered, and the filtrate was washed with 5% aqueous sodium bicarbonate, dried over magnesium sulfate, and evaporated under reduced pressure. The residue was dissolved in 20 mL of a mixture of trifluoroacetic acid and methylene chloride, 1:1, and stirred for one hour at room temperature. The solvents were removed under reduced pressure, and the residue was dissolved in methylene chloride (about 20 mL), and an excess of HCl in methanol was added and allowed to stand at room temperature for 30 minutes. The solvents were removed under reduced pressure, and the residue was crystallized from methanol:ethanol. The yield was 85%, mp 238°–240° C., $^1$H-NMR (DMSO) 4.2 (q, 2,—COCH$_2$), Anal: C, H, N, Cl.

Example 2

Camptothecin-20-O-(N,N-diethyl)glycinate.HCl (Formula 10)

First 20-O-chloroacetyl camptothecin was formed from a mixture of 3.48 grams (10 mmole) of camptothecin, 2.05 grams (12 mmole) chloroacetic anhydride, 0.805 mL (10 mmole) pyridine, and 0.122 gram (1 mmole) of 4-dimethylaminopyridine in 200 mL of freshly distilled (from P$_2$O$_5$) chloroform was stirred under reflux for three hours. The reaction mixture was cooled to room temperature and washed successively with water, 0.1N NaOH, and with water. The organic extract was dried over anhydrous sodium sulfate, and the solvent was removed under reduced pressure to give the chloroacetate as a pale yellow crystalline solid. The yield was 4.10 grams (96.5%). The solid was used in the next step without any purification.

20-O-iodoacetyl camptothecin

The crude chloroacetate from above was dissolved in 500 mL of acetone by heating on a steam bath. The solution was cooled to room temperature, and 6 grams (40 mmole) of sodium iodide was added. The mixture was stirred and refluxed under nitrogen atmosphere for four hours. The precipitated sodium chloride was removed by filtration and washed with 100 mL of acetone. The combined filtrates were evaporated to dryness under reduced pressure, and the residue was partitioned between chloroform (300 mL) and water (100 mL). The organic layer was washed six times with water, dried over sodium sulfate, and evaporated under reduced pressure to give a pale yellow crystalline solid. The solid was recrystallized from methylene chloride:-methanol to give 4.1 grams (79.5% from 1) of pure iodoacetate, mp 238°–240° C. 1R (Nujol) 1760–1745 cm$^{-1}$ (lactone and ester), 1600 cm$^{-1}$ (lactam); NMR (CDCL$_3$) 3.8 (2H, S, COCH$_2$I).

20-O-(N,N-diethyl)glycinyl camptothecin:

The iodoacetate (1.032 grams, 2 mmoles) from above was dissolved in 200 mL of chloroform, 1.028 mL (10 mmole) of diethylamine was added, and the solution was stirred for 45 minutes at room temperature. The solvents were removed under reduced pressure, and the residue was partitioned between chloroform and water, 100 mL each. The chloroform layer was washed three times with water, dried over anhydrous sodium sulfate, and evaporated to dryness under reduced pressure. The resulting pale yellow residue, 0.85 gram, 92% yield, was dissolved in 50 mL of dry chloroform, and an excess of methanolic HCl was added. The solution turned bright yellow. After standing at room temperature for 30 minutes, the solvents were removed under reduced pressure, and the residue was crystallized from methanol:-water. The product was recrystallized from absolute ethanol to give an analytically pure compound. The yield was 0.7 gram, 76.3%, mp 223–224. $^1$H-NMR (DMSO-d6) 4.6 [q, 2, COCH$_2$N(C$_2$H$_5$)$_2$], IR (Nujol) 1760 cm−1 (ester and lactone). Analysis: C, H, N, Cl.

Example 3

Camptothecin-20-O-hemisuccinate sodium salt (Formula 14):

A mixture of 100 mg, mole camptothecin, 34 mg, succinic acid, 62 mg, dicyclohexylcarbodiimide, and 3.6 mg, 4-dimethylaminopyridine were suspended in methylene chloride and stirred for six hour at room temperature. The mixture was filtered, and the filtrate was evaporated to dryness under reduced pressure. The residue was dissolved in a mixture of chloroform and acetone (75:25) and chromatographed on silica gel. Fractions containing the desired product (Rf 0.53, Analtech GLH Plates developed in the eluting solvent system) were combined and evaporated under reduced pressure. The residue was suspended in distilled water and titrated to pH 8.0 with 1N NaOH. The resulting solution was freeze-dried to obtain a solid product. The yield was 80%, mp 235°–238° C.; $^1$H-NMR (D$_2$O) 2.3–2.44 (m, 4, CH$_2$CH$_2$COONa); Analysis: C,H,N.

Example 4

Camptothecin-20-phosphate sodium salt (Formula 15):

Camptothecin (100 mg, 0.287 mole) was suspended in 50 mL of tetrahydrofuran, the the mixture was cooled to −20° C. with stirring. To this mixture was added 1 mL of pyrophosphoryl tetrachloride (prepared according to Crafts et al., J. Chem. Soc., 1960, 3673) was added, and stirring was continued for two hours. The reaction mixture was then poured into ice water, and the solvents were removed under reduced pressure. The residue was crystallized from ethanol to yield 90% camptothecin-20-phosphate as the free acid. The acid was suspended in water and titrated to pH 7.5 with 1N NaOH, and the resulting solution was lyophilized to give the sodium salt as a fluffy solid, mp 210°–213° C. Analysis: C,H,N.

The camptothecin derivatives of the present invention can be administered to a patient suffering from cancer at a dosage rate to provide a dose of camptothecin of from about 0.5 to about 10.0 mg/kg of body weight. The compounds can be administered in a sequence of doses, e.g., one dose every two weeks. Therapy is repeated until definite disease progression is halted.

A preferred method of administration of the compounds of the present invention is by rapid intravenous injection over a five-to fifteen-minute period.

The formulations for administering the compounds of the present invention may be any formulation compatible with the active ingredient. The formulations may, where appropriate, be conveniently presented in discrete dosage units and may be prepared by any of the methods well known in the art of pharmacy.

The pharmaceutical formulations may include any suitable carrier ingredients such as buffers, diluents, surfactants, lubricants, preservatives (including antioxidants) and the like, as well as substances included for the purpose of rendering the formulation isotonic with the blood of the intended recipient.

Alternatively, the compounds of the present invention can be administered parenterally in aqueous solution at a dosage rate to provide effective amounts of camptothecin, generally of from about 0.5. to about 10.0 mg/kg of body weight.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology employed herein is for the purpose of description and not of limitation.

What is claimed is:

1. A compound of the formula:

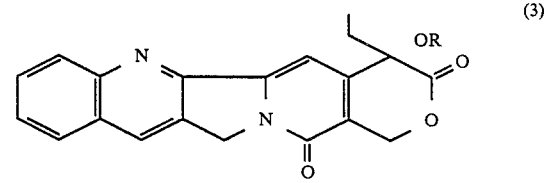

(3)

wherein R is selected from the group consisting of:
R=CO CH₂ NH₂.HCl
R=CO CH₂NHCH₃.HCl
R=CO CH₂NHC₂H₅.HCl
R=CO CH₂ N(C₂H₅)₂.HCl
R=CO CH(NH₂) CH₂CH₂CH₂CH₂CH₂NH₂.2HCl
R=CO CH(NH₂) CH₂CH₂COOH. HCl
R=CO CH₂CH2.COO⁻ Na+.

2. A method for administering camptothecin to a patient in need of camptothecin comprising administering to said patient an aqueous solution of a compound of claim 1.

3. A method of treating cancers which can be treated by administering camptothecin comprising administering to a patient with cancer an aqueous solution of a compound of claim 1 in sufficient quantity to provide from about 5 to about 10.0 mg/kg of body weight of camptothecin.

* * * * *